(12) United States Patent
Mantlo et al.

(10) Patent No.: US 11,291,986 B2
(45) Date of Patent: Apr. 5, 2022

(54) UNIQUE SAMPLE TRANSFER DEVICE FOR AN AUTOMATED PIPETTOR FOR PROCESSING A VARIETY OF CLINICAL MICROBIOLOGICAL SPECIMENS

(71) Applicant: BECTON DICKINSON AND COMPANY, Franklin Lakes, NJ (US)

(72) Inventors: John D. Mantlo, Sykesville, MD (US); Tong Zhou, Ellicott City, MD (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 387 days.

(21) Appl. No.: 15/903,767

(22) Filed: Feb. 23, 2018

(65) Prior Publication Data
US 2018/0243735 A1    Aug. 30, 2018

Related U.S. Application Data

(60) Provisional application No. 62/463,177, filed on Feb. 24, 2017.

(51) Int. Cl.
*B01L 3/02* (2006.01)
*C12Q 1/24* (2006.01)
(Continued)

(52) U.S. Cl.
CPC .............. *B01L 3/021* (2013.01); *B01L 3/0275* (2013.01); *C12Q 1/24* (2013.01); *G01N 35/0099* (2013.01);
(Continued)

(58) Field of Classification Search
None
See application file for complete search history.

(56) References Cited

U.S. PATENT DOCUMENTS 6,702,990 B1 *   3/2004   Camacho .............. B01L 3/0217
                                                                                 204/613
8,114,027 B2   2/2012   Triva
(Continued)

FOREIGN PATENT DOCUMENTS

EP          0643131 B1      7/2001
WO       2006063979 A1     6/2006
(Continued)

OTHER PUBLICATIONS

"Getting Started with CapSense®", Cypress Semiconductor, pp. 127.
(Continued)

*Primary Examiner* — Matthew D Krcha
*Assistant Examiner* — Brittany I Fisher
(74) *Attorney, Agent, or Firm* — Botos Churchill IP Law LLP

(57) ABSTRACT

The present disclosure describes pipette tips having an absorbent material (e.g., a flocking material) anchored to a distal end of the pipette tip and related methods of use. In some embodiments, the flocked pipette tips can be used in an automated process and/or system, wherein the contact between the pipette tips and either a sample or a culture medium can be automatically sensed for accurate sample collection and/or dispense. In some embodiments, automatic detection of the liquid interface may be accomplished by detecting a threshold change in capacitance when the pipette tip contacts the sample liquid interface (e.g., for sample collection) or the agar interface (e.g., for sample release). In some embodiments, the automated process and/or system may utilize one or more predetermined, fixed heights for collecting samples and/or depositing samples.

3 Claims, 5 Drawing Sheets

(51) Int. Cl.
*G01N 35/00* (2006.01)
*G01N 35/10* (2006.01)
*G01N 1/12* (2006.01)
*G01N 1/02* (2006.01)

(52) U.S. Cl.
CPC ....... *G01N 35/00584* (2013.01); *G01N 35/10* (2013.01); *B01L 2300/069* (2013.01); *B01L 2300/0627* (2013.01); *B01L 2400/0487* (2013.01); *G01N 1/12* (2013.01); *G01N 2001/028* (2013.01); *G01N 2035/103* (2013.01); *G01N 2035/1027* (2013.01)

(56) References Cited

U.S. PATENT DOCUMENTS

| | | | |
|---|---|---|---|
| 8,631,715 B2 | 1/2014 | Triva | |
| 9,170,177 B2 | 10/2015 | Triva | |
| D772,398 S | 11/2016 | Triva | |
| 9,504,452 B2 | 11/2016 | Triva | |
| 2005/0042138 A1* | 2/2005 | Ueda | B01L 3/50825 422/63 |
| 2009/0048534 A1 | 2/2009 | Triva | |
| 2010/0083773 A1* | 4/2010 | Schmiedl | B01L 3/0275 73/864.01 |
| 2010/0218622 A1* | 9/2010 | Motadel | B01L 3/0279 73/864.01 |
| 2010/0219093 A1* | 9/2010 | Motadel | B01L 9/543 206/443 |
| 2011/0183433 A1* | 7/2011 | Motadel | B01L 3/0279 436/180 |
| 2013/0344616 A1 | 12/2013 | Triva | |
| 2014/0017804 A1 | 1/2014 | Triva | |
| 2014/0242570 A1* | 8/2014 | Botma | G01N 35/1011 435/3 |
| 2015/0276566 A1* | 10/2015 | Berntsen | G01N 1/312 435/309.1 |
| 2016/0184815 A1 | 6/2016 | Triva | |
| 2016/0367227 A1 | 12/2016 | Triva | |
| 2017/0023446 A1* | 1/2017 | Rietveld | A61B 5/150358 |

FOREIGN PATENT DOCUMENTS

| | | |
|---|---|---|
| WO | 2006131423 A1 | 12/2006 |
| WO | 2011095599 A1 | 8/2011 |
| WO | 2012000734 | 1/2012 |
| WO | 2015052607 | 4/2015 |
| WO | 2016164712 | 10/2016 |
| WO | 201619646 | 12/2016 |

OTHER PUBLICATIONS

Walser, Dr. Rudolf, "LLS—Liquid Level Sensing methods in qPCR set-up", pp. 16.

* cited by examiner

UNIQUE SAMPLE TRANSFER DEVICE FOR AN AUTOMATED PIPETTOR FOR PROCESSING A VARIETY OF CLINICAL MICROBIOLOGICAL SPECIMENS

CROSS-REFERENCE TO RELATED APPLICATIONS

This application claims the benefit of U.S. Provisional Patent Application No. 62/463,177, filed Feb. 24, 2017, which is incorporated herein by reference.

BACKGROUND

In the field of clinical and diagnostic analyses, swabs for collecting biological specimens of organic material are known, consisting essentially of a cylindrical rod around one end of which, known as the tip, is wrapped a wad of fiber, such as rayon or a natural fiber such as cotton, with hydrophilic properties to allow rapid absorption of the quantity of specimen to be collected and tested. Stable adherence of the fiber wrapped around the tip of the rod is generally achieved by gluing.

Usually, especially if the specimen is to be examined by culturing the microorganisms gathered with the collection, a swab is immersed in a test-tube containing culture medium immediately after collection for appropriate conservation of the specimen during storage and/or transport thereof to the analytical laboratory. In other methods, the swab is placed in a vessel for transport. When received, the swab is streaked over agar in a petri dish, thereby inoculating the agar with the sample.

Examples of devices used in these methods are found in European Patent No. 0643131 ("the '131 Patent") and U.S. Pat. No. 8,114,027 ("the '027 Patent"), which describe swabs for collecting and in vitro transporting specimens. The '131 Patent describes a test-tube with culture medium in gel form and a rod carrying at one end a stopper for sealing the test-tube and at the opposite end means for collecting said specimen, for example a wad of fiber wrapped around the tip of the rod, to be dipped into the culture medium. Such swabs are often referred to as flocked swabs. The '027 Patent describes flocked swabs that have hydrophilic fibers that collect sample efficiently and also release the sample efficiently when the inoculated swab is spread onto culture medium (e.g., agar). The descriptions of the '131 Patent and the '027 Patent are incorporated by reference herein.

One of the disadvantages is that such flocked swabs are handled manually. Automated methods for collecting sample and releasing sample using flocked swabs continue to be sought.

BRIEF SUMMARY

The present disclosure describes pipette tips having an absorbent material (e.g., a flocking material) anchored to a distal end of the pipette tip and related methods of use. In some embodiments, the flocked pipette tips can be used in an automated process and/or system, wherein the contact between the pipette tips and either a sample or a culture medium can be automatically sensed for accurate sample collection and/or dispense. In some embodiments, automatic detection of the liquid interface may be accomplished by detecting a threshold change in capacitance when the pipette tip contacts the sample liquid interface (e.g., for sample collection) or the agar interface (e.g., for sample release). In some embodiments, the automated process and/or system may utilize one or more predetermined, fixed heights for collecting samples and/or depositing samples. In some embodiments the interface is detected due to contact between the pipette tip and the underlying surface (e.g., an agar or a solid sample). In these embodiments, the pipette tip is not further advanced by the pipettor once the tip encounters some sort of force impeding its descent.

One aspect of the present disclosure relates to a pipette tip comprising: (a) an elongated body having a proximal end and a distal end; (b) an interface at the proximal end of the elongated body for engaging a robotic pipettor; and (c) flocking material anchored to the distal end of the elongated body. In some embodiments, the flocking material comprises hydrophilic fibers. In some embodiments, the flocking material comprises cotton. In some embodiments, the flocking material is anchored to the distal end of the pipette tip through the use of an adhesive. In some embodiments, the elongated body is constructed of a conductive material.

Another aspect of the present disclosure related to a system comprising: (a) a robotic pipettor having a capacitance sensor, wherein the robotic pipettor is configured to hold one or more pipette tips; (b) a conductive pipette tip having an absorbent material anchored to a distal end of the conductive pipette tip; and (c) a capacitance detecting circuit configured to detect contact between the conductive pipette tip when a signal from the capacitance sensor exceeds a predetermined threshold. In some embodiments, the absorbent material is a flocking material. In some embodiments, the flocking material comprises hydrophilic fibers. In some embodiments, the flocking material comprises cotton. In some embodiments, the flocking material is anchored to the distal end of the pipette tip through the use of an adhesive.

Yet another aspect of the present disclosure relates to a method comprising: (a) attaching a pipette tip to a robotic pipettor, wherein the pipette tip comprises; (i) an elongated body having a proximal end and a distal end; (ii) an interface at the proximal end of the elongated body for engaging the robotic pipettor; and (iii) flocking material anchored to the distal end of the elongated body; (b) lowering, with the robotic pipettor, the pipette tip of claim 1 into a sample container until at least some of the flocking material is submersed in a liquid sample in the sample container; (c) waiting a period of time for the flocking material to absorb some of the liquid sample; and (d) inoculating, with the robotic pipettor, an agar in a petri by streaking the flocking material over the agar in the petri dish. In some embodiments, the method further comprises applying, with the robotic pipettor, a negative pressure to draw some of the liquid sample into the pipette tip while at least some of the flocking material is submersed in the liquid sample. In some embodiments, the method further comprises applying, with the robotic pipettor, a positive pressure to dispense some of the liquid sample in the pipette tip before inoculating the agar.

DETAILED DESCRIPTION

Described herein are flocked pipette tips that are used with robotic pipettor mechanisms. In some embodiments, the flocked pipette tips are used to collect samples, wherein the robotic mechanism moves the pipette tip over a location of the sample and lowers the pipette tip into contact with the sample. In some embodiments, the flocked pipette tips are lowered to one or more predetermined, fixed heights for collecting and/or dispensing one or more samples. The one or more predetermined, fixed heights are based on one or more of the expected dimensions of a sample collection tube, a petri dish, and/or the thickness of an agar in a petri dish. One skilled in the art is aware of other fixed height such as height of sample in a collection tube with known dimensions and known sample quantity. In one exemplary embodiment, one predetermined, fixed height corresponds to a position wherein the flocked pipette tube is immersed in a sample within a sample collection tube. As another example, one predetermined, fixed height corresponds to a position wherein the flocked pipette tube barely contacts the surface of an agar in a petri dish.

In some embodiments, the pipette tip is conductive and a capacitance sensor is provided with robotic pipettor mechanisms for sensing contact between the flocked pipette tips and either a sample or a culture medium. Capacitance sensors, robotic mechanisms for acquiring and using pipette tips to collect and dispense such samples, and conductive pipette tips themselves are well known to one skilled in the art and are not described in detail below.

In yet another embodiment (referred to as "Z-stall") the interface is detected due to some physical contact between the pipette tip and the underlying surface (e.g., agar, semi-solid sample, solid sample, etc.). In these embodiments, the pipette tip is not further advanced by the robotic pipettor once the tip encounters some sort of force impeding its descent.

Figure 1:
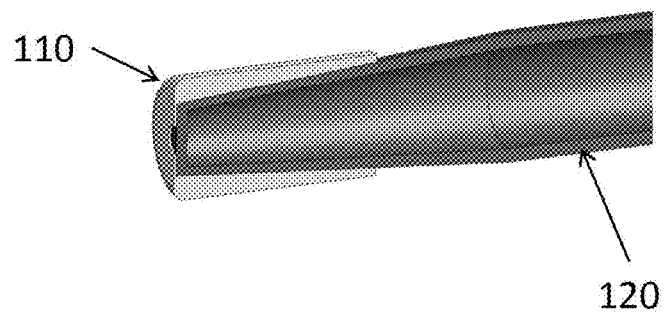
FIG. 1 illustrates a flocked pipette tip according to one embodiment of the present invention in cross-sectional view.
Figure 2:
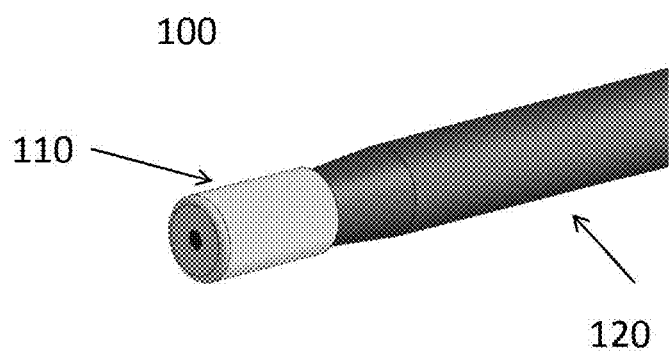
FIG. 2 illustrates a flocked pipette tip according to one embodiment of the present invention in full view.
Figure 3C:
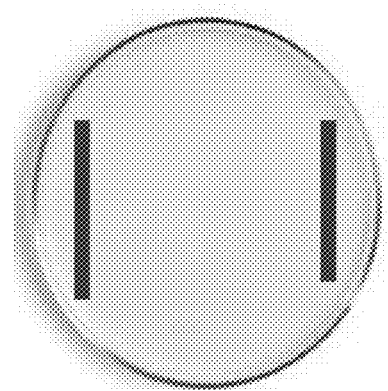
FIGS. 3A-C illustrate the distribution of sample on an agar plate using the flocked pipette tip described herein as controlled by a robotic mechanism with distribution in an x-y direction.
Figure 3B:
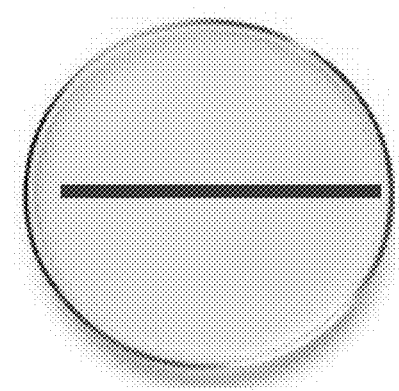
Figure 3A:
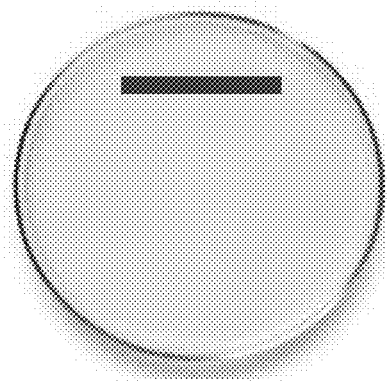
Figure 4C:
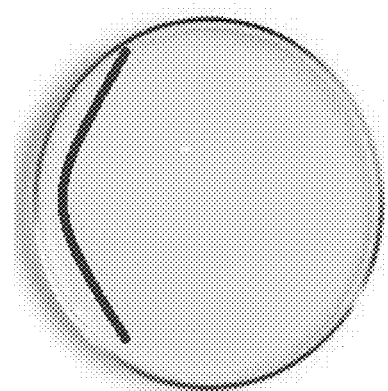
FIGS. 4A-C illustrate the distribution of sample using the pipette tip described herein with robotic control in the x-y direction accompanied by plate rotation.
Figure 4B:
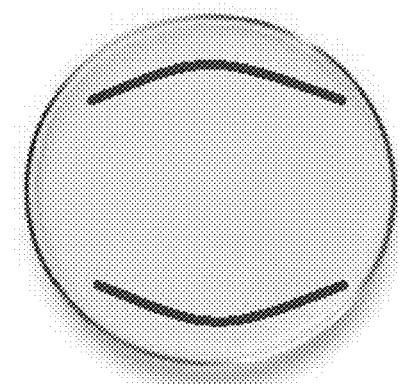
Figure 4A:
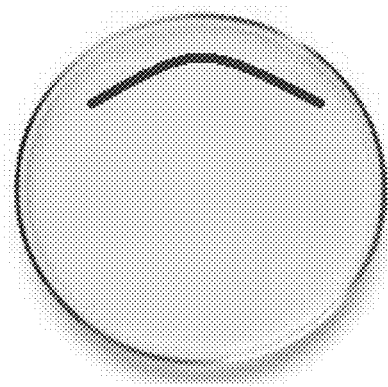

FIGS. 1 and 2 illustrate a flocked pipette tip according to one embodiment of the present invention. As shown, the flocked pipette tip 100 includes flocking 110 and a pipette tip 120. In some embodiments, the pipette tip is conductive. In some embodiments, the flocking 110 comprises a wad of fiber, such as rayon or a natural fiber such as cotton, with hydrophilic properties to allow rapid absorption of a sample. In some embodiments, the flocking 110 is attached to a distal end of the pipette tip 120 through the use of an adhesive. In some embodiments, the flocked pipette tip 100 is used to collect semi-liquid and/or solid specimens. As a result, the flocked pipette tip 100 can facilitate fully-automated processing of clinical specimens.

In some embodiments, the flocked pipette tip described herein is used in an automated system, such as BD Kiestra's InoqulA. InoqulA™ is a trademark of BD Kiestra. In one embodiment, a standard capacitive pipette tip that fits the current InoqulA™ Hamilton pipettor, having an absorbent material (e.g., a flocking material) anchored or otherwise attached to a distal end of the tip is contemplated. Using the current InoqulA™ workflow, the flocked pipette tip is lowered into a specimen tube until it contacts a sample contained therein and a capacitance feature is triggered stopping the downward movement of the pipette tip. The flocked pipette tip is then immersed into the specimen tube to a set z-value and held for a time to allow the flocked material to absorb the sample. The flocked pipette tip containing the sample is then removed from the specimen tube and moved to the inoculation area. Once again, using the Hamilton capacitance feature, the flocked pipette tip is lowered to apply the sample to a plate, broth tube or other collection device. When sample addition is complete, the flocked pipette tipis moved over a biohazard waste bin and ejected.

The use of pipette tips to collect sample is described in International Publication Nos. WO 2016/191646 ("the '646 Publication") and WO 2016/164712 ("the '712 Publication"), which are incorporated by reference herein. One method of determining the contact, between a liquid interface and a pick tool is described in U.S. Patent Publication No. 2014/0242570 ("the '570 Publication"), which is incorporated herein by reference.

In one embodiment, for dispense, an automated system uses a flocked pipette tip to position the inoculum to provide an improved streaking pattern. The flocked pipette tip provides an improvement over dispensing liquid on an agar plate and dispersing it, which can be negatively affected by several factors, such as volume (e.g., larger volumes may spread out more and irregularly), placement area (e.g., near plate edge) and agar contour (e.g., a level agar versus an agar having peaks and valleys). Application of the inoculum by the flocked pipette permits better placement of a specimen by using capacitance detection followed by plate rotation or pipette movement (e.g., x or y movement) to add the sample to the chosen areas. Examples of such streaking trajectories are illustrated in FIGS. 3A-C and 4A-C.

In one embodiment, a robotic pipettor of an automated system is fitted with a CapSense® Liquid Level Sensing system. CapSense is a registered trademark of Cypress Semiconductor. Such a detector indicates contact with a liquid interface by a change in capacitance between two electrodes (here the two electrodes are the conductive pipette tip and an ionic surface (e.g., the surface of an aqueous liquid). Capacitance liquid contact sensing is a known technique. A capacitance detection circuit measures the capacitive potential between the two conductive surfaces in close proximity and electrically isolated by a non-conductor (e.g., air). In the context of the described embodiments, the nonconductor is air. When a voltage or potential is applied to the circuit, the two conductors are at different potentials and the system stores an electric charge.

Figure 5:
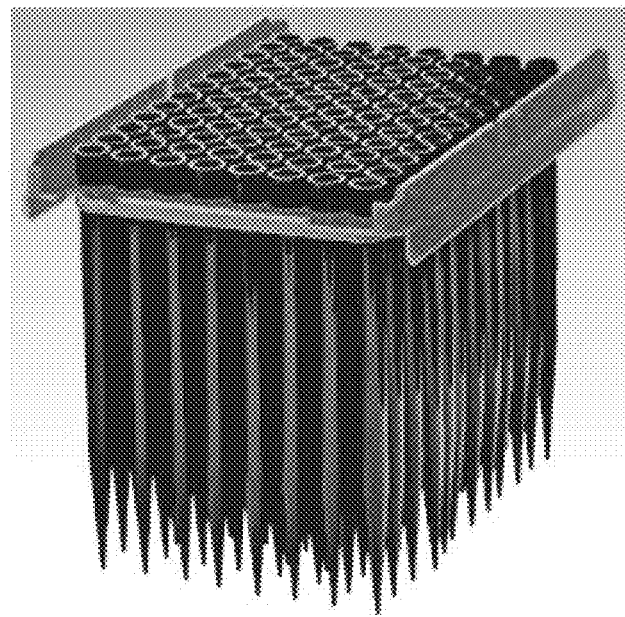
FIG. 5 illustrates commercially available conductive pipette tips.

One example of a suitable conductive robotic pipette tip is BLACKKNIGHTS which is commercially available from Ritter Medical. Such pipette tips are configured for use on commercially available workstations (e.g., robotic mechanisms for collating and dispensing samples using a robotic pipettor from Hamilton, Tecan, Qiagen, Olympus, etc.). An example of such pipette tips is illustrated in FIG. 5. In one embodiment, the pipette tips are conductive because they are made of carbon black conductive polypropylene.

In one exemplary embodiment, flocking material is anchored to pipette tips, such as the ones illustrated in FIG. 5, using one or more methods described in the '027 Patent, wherein hydrophilic fibers are placed in contact with pipette tips in an electrostatic field that deposits the fibers in an ordered manner, for example, orthogonal (e.g., roughly perpendicular) to the surfaces of the pipette tips. For example, the pipette tips are coated with adhesive either by immersion or spraying, prior to being placed in contact with the fibers. The fibers are thereby deposited in an oriented manner and anchored to the surface of the pipette tip, being retained by the adhesive. In one example, the adhesive is water-based. Drying the adhesive anchors the fibers thereon. The flocked swab is then dried by exposing it to a source of heat or radio-frequency. The fiber dimensions are largely a matter of design choice and can be of the sort described in the '027 Patent. The skilled person is able to select fiber materials and dimensions that suit their particular need. Such selection is within the abilities of a person skilled in the art.

The '712 Publication is commonly owned with the present application and describes the use of a pipette tip as a pick tool for collecting microorganisms grown on a semisolid surface for preparation of a suspension of microorganisms in a liquid solution that can be used for further identification (e.g., using MALDI or other technique) and/or AST testing.

Although many of the embodiments described herein recite an automated system with a robotic pipettor for carrying a conductive pipette tip, the pipette tip is used to acquire the sample by aspiration in some embodiments and in other embodiments the pipette tip is used to acquire the sample by pressing the pipette tip against or into the sample. The robotic pipettor is used to move the pipette tip into contact with the sample to acquire the sample and dispense the sample. In some embodiments the robotic pipettor does not aspirate the sample into the pipette tip but may cause air to flow out the pipette tip to assist in sample dispense. In all embodiments the pipette tip is flocked to enhance both sample collection and sample release. As a result, in some embodiments, as noted above, the robotic pipettor does not aspirate the sample into the flocked pipette tip. However, in other embodiments, it is contemplated that negative pressure might be used to draw samples into the flocked pipette tip. Whether or not the robotic pipettor aspirates sample into the flocked pipette tip, in either of those embodiments a positive pressure can be subsequently applied to dispense some of the sample in the pipette tip. However, in other embodiments, the robotic pipettor acquires sample in the various ways described herein but does not deploy positive pressure sample dispense.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method comprising:
    attaching a pipette tip to a robotic pipettor, wherein the pipette tip comprises:
        a pipette tip having a proximal end and a distal end wherein the pipette tip is constructed of a conductive material;
        an interface at the proximal end of the conductive pipette tip for engaging the robotic pipettor; and
        flocking material anchored to the distal end of the conductive pipette tip wherein the flocking material is absorbent fibers fixed on a surface of the distal end of the conductive pipette tip in an ordered manner;
    lowering, with the robotic pipettor, the conductive pipette tip into a sample container until at least some of the flocking material is submersed in a liquid sample in the sample container;
    waiting a period of time for the flocking material to absorb some of the liquid sample; and
    inoculating, with the robotic pipettor, an agar in a petri dish by streaking the flocking material over the agar in the petri dish while simultaneously detecting contact between the conductive pipette tip and the agar.

2. The method of claim 1 further comprising:
    applying, with the robotic pipettor, a negative pressure to draw some of the liquid sample into the conductive pipette tip while at least some of the flocking material is submersed in the liquid sample.

3. The method of claim 2 further comprising:
    applying, with the robotic pipettor, a positive pressure to dispense some of the liquid sample in the conductive pipette tip before inoculating the agar.

* * * * *